United States Patent [19]

Wasko

[11] 4,021,866
[45] May 10, 1977

[54] HAND PROSTHESIS

[76] Inventor: Joseph L. Wasko, Rte. 1, Buhl, Idaho 83316

[22] Filed: Sept. 27, 1976

[21] Appl. No.: 726,934

[52] U.S. Cl. ............................... 3/12; 3/12.8
[51] Int. Cl.² ......................................... A61F 1/06
[58] Field of Search ............................. 3/12–12.8

[56] References Cited

UNITED STATES PATENTS

| | | | |
|---|---|---|---|
| 1,263,675 | 4/1918 | Jeffery | 3/12.8 |
| 1,322,027 | 11/1919 | Lacaire | 3/12.8 |
| 1,498,029 | 6/1924 | Giles | 3/12 |
| 3,434,163 | 3/1969 | Saverino | 3/12.8 |
| 3,526,006 | 9/1970 | Beardmore | 3/12.8 |

FOREIGN PATENTS OR APPLICATIONS 459,255   9/1950   Italy ................................ 3/12.8

*Primary Examiner*—Ronald L. Frinks
*Attorney, Agent, or Firm*—Wells, St. John & Roberts

[57] ABSTRACT

A hand prosthesis to be utilized in conjunction with an arm that has at least one functional joint and a movable portion of the arm outward of the joint. The prosthesis includes a base that is strapped to the user inwardly adjacent to the functional joint. A pair of plates are hinged at rearward ends and mounted to the base by a ball and socket arrangement. The ball and socket connects one plate to the base while the remaining plate is releasably fastened to the movable portion of the arm. Thus, the base acts as a relatively stationary support for the one plate while the remaining plate may be selectively pivoted about the axis of the hinge to open or close the plates in response to movement of the movable arm portion.

8 Claims, 4 Drawing Figures

HAND PROSTHESIS

BACKGROUND OF THE INVENTION

The present invention is related to prosthetic devices and more particularly to such devices utilized to replace an amputated or mutilated hand.

A person who has suffered the loss of a major portion of his hand while retaining a movable part thereof is severely restricted to the forms of prosthetic devices he may utilize to regain gripping control through the affected arm. Most prior hand prostheses are produced and designed for amputees whose complete hand is missing. It is therefore desirable to obtain some form of prosthesis that may capitalize on the movements capable of an arm member (a portion of the hand) existing outward of a functional joint to produce a gripping force through the prosthetic device.

U.S. Pat. No. 3,526,006 to R. L. Beardmore granted Sept. 1, 1970 discloses a wrist extensor operated hand splint. The purpose for this splint is to enable certain persons who have suffered back injuries and have lost the use of one or both hands to produce a gripping force through a splint device attached between the movable portions of the forearm and hand. This device is comprised of two separate specially designed plates. A first plate substantially fits the cupped hand and includes an inwardly extending (toward the elbow) base. This base pivotably mounts to the second member which includes opposed arm clasping surfaces and an outwardly projecting gripping surface. Also included is a pedestal to which the individual members are mounted to facilitate mounting and removal of the members to a user's arm. Gripping force is produced through the two independent members by movement of the user's wrist. The device mounts to specific portions of the user's hand and would not operate efficiently in conjunction with a partially amputated or mutilated hand.

U.S. Pat. No. 3,434,163 to P. Saverino issued Mar. 25, 1969 discloses a prosthetic holder for use with a mutilated or deformed hand. Saverino basically shows a holding device that is strapped to a user's wrist and which is stationary with respect to a movable portion of the hand such as a thumb. The mounting plate is strapped to the wrist on the same side as the the thumb. A portion of the mounting member extends across the hand area to mount the plate against which the thumb may act. Different devices may be attached to the plate to facilitate actions other than gripping between the plate and thumb.

Other patents of interest are U.S. Pat. Nos. 3,735,426; 1,498,029; 1,322,027; and 1,263,675.

Of the above devices, none disclose the pivoted arrangement of two hinged plates pivotably mounted to a relatively stationary base, in which the base may be mounted stationary relative to the pivoted plate members and the plate members attach to a movable portion of a user's arm to the outward side of a functional joint such that the movable portion may be operated against the pivoted plates to move the plates between an open and closed position and further to pivot the plates about the connection between the plates and the pivoted base support.

SUMMARY OF THE INVENTION

A hand prosthesis is described for use with an arm having a functional joint and a movable portion of the arm outward of the joint. The prosthesis includes an elongated base member with a first strap means thereon for securely mounting the base member to a user in a stationary relationship to the movable arm portion. First and second elongated plates are provided that have inward and outward ends. The plates are interconnected at their inward ends by a hinge means and mounted to the base member through a mounting means. The mounting means is situated to pivotably connect the first plate to the base member with the hinge means situated between the mounting means and first strap means. A second strap means is fastened to the second plate for mounting the second plate to the movable portion of the arm.

It is a primary object of the present invention to provide a hand prosthesis which will enable a user to perform gripping functions similar to that of a normal hand by utilizing only a small portion of the arm outwardly adjacent a joint thereof.

Another object is to provide such a prosthesis that is very simple in construction, easy to manufacture, and therefore inexpensive to purchase.

A still further object is to provide such a prosthesis that is substantially universal in that it may be adapted to different size arms and different physical conditions.

These and yet further objects and advantages will become apparent upon reading the following detailed description which, taken with the accompanying drawing, disclose a preferred form of my invention. However, it is not intended that the specification be taken as restrictive to the scope of my invention. Only the claims to be found at the end of this specification are to be taken as restrictions upon the scope of my invention.

DETAILED DESCRIPTION OF A PREFERRED EMBODIMENT

Figure 1:
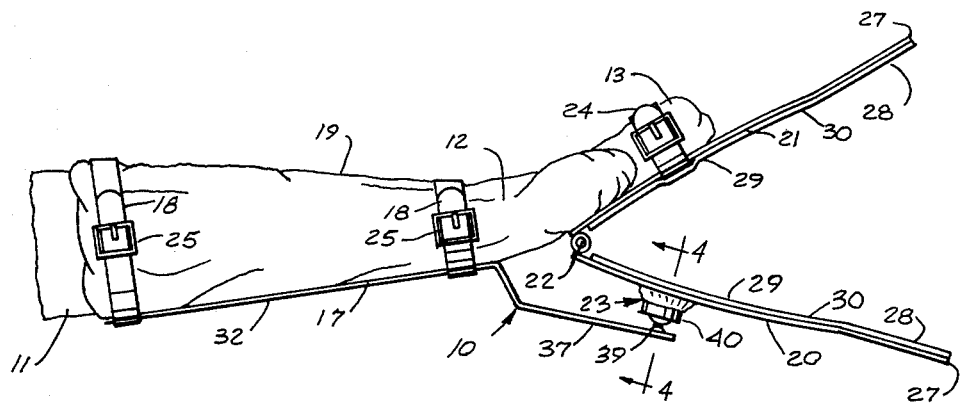
FIG. 1 is a fragmentary side elevation view of the present prosthesis mounted to an arm.

A prosthesis embodying elements of the present invention is illustrated in the accompanying drawings and is designated generally therein by the reference character 10. The prosthesis 10 is specifically designed for use on an arm 11 that includes at least one flexible, functional joint 12, and a movable portion 13 of the arm extending outwardly from the joint area 12. Thus, the arm portion shown could be the forearm area and the joint area 12 be the wrist articulation. The movable portion 13 would then be any part of a hand extending outwardly of the wrist.

It is only required that the joint area 12 be movable and that a movable portion of the bone structure connected therewith protrude outwardly from the joint to facilitate operation of the present invention. It should be noted that although the primary intended use is in such situations wherein the prosthesis 10 is utilized to replace a hand and is operated by a portion of the hand that the same prosthesis structure could be attached to a user's upper arm and the elbow joint used as the point of articulation. In this case, a portion of the forearm would serve to operate the gripping elements of the present prosthesis 10.

Prosthesis 10 is basically comprised of an elongated base 17 that is held by means of a pair of straps 18 to the user's arm 11. A glove 19 may be placed on the user's arm prior to placement of the prosthesis 10. Such a fabric glove 19 will function to prevent chafing of the user's skin beneath the several straps that connect the prosthesis to the arm.

The gripping elements of prosthesis 10 include a first plate 20 that is connected to a second plate 21 by means of a hinge 22. The hinge 22 is located at inward ends of plates 20 and 21. A mounting means 23 is situated between the first plate 20 and base 17 to movably mount the plates to the base 17. Another strap 24 interconnects the second plate 21 with the movable arm portion 13.

The straps 18 and 24 are flexible leather straps that include integral buckles 25. The buckles and straps may be adjusted to accommodate arms of different size.

Figure 2:
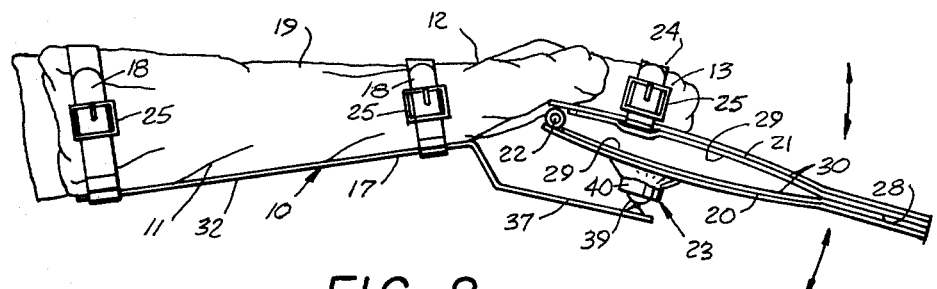
FIG. 2 is a view similar to FIG. 1 only showing the plates of the prosthesis in a closed condition.

It may be noted in FIGS. 1 and 2 that the strap 24 and mounting means 23 are situated outwardly of the hinge 22. Further, the hinge 22 is situated closely adjacent to the joint area 12. This facilitates forceable pivotal movement of the plates from an open position as shown in FIG. 1 to the closed position of FIG. 2. This movement, since the axis of hinge 22 is close to the joint 12, does not produce relative longitudinal movement between the movable arm portion 13 and plate 21.

Figure 3:
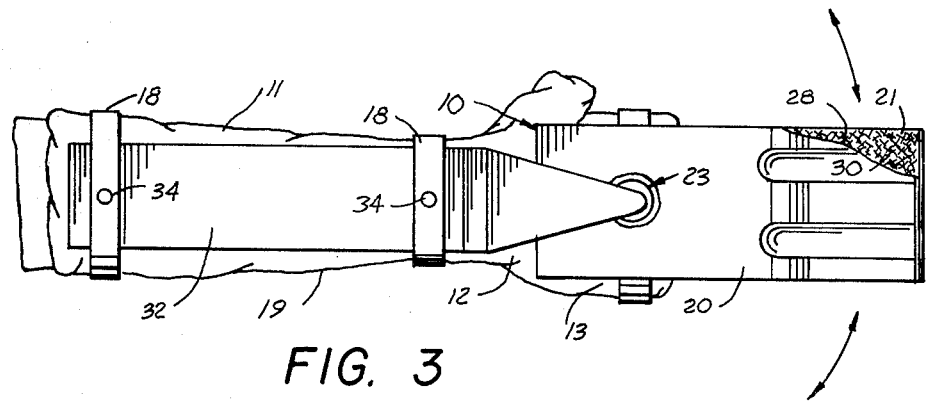
FIG. 3 is a bottom plan view as seen from below in FIG. 2.

The plates 20 and 21 include free outer ends 27 that, as shown in FIGS. 2 and 3, are complementary and include facing gripping surfaces 28. Surfaces 28 abut one another when the plates are in the closed position. The plates also include opposed facing concave surfaces 29 that extend inward of the gripping surfaces 28 to the hinge means 22. The two gripping configurations presented by surfaces 28 and 29 facilitate gripping of different size objects.

To further facilitate gripping and holding of objects, a frictional covering 30 is provided along the surfaces 28 and 29. A portion of the covering 30 is illustrated in FIG. 3. The material comprising covering 30 may vary with the intended use of the present prosthesis. However, it is desirable to have some form of slightly frictional surface such as rubber for frictional gripping.

The base 17 is comprised of an elongated flange 32 that carries the first strap means 18. The strap 18 are separated longitudinally and are mounted by rivets 34 to the flange 32. Thus, the flange portion 32 of base 17 may be mounted in a stationary condition relative to the arm 11. The outward end of base 17 includes an angular offset 37 that extends beyond the joint area 12 to the mounting means 23. This offset is important to proper functioning of the present prosthesis. It enables pivotal movement of the plates 20 and 21 in substantially any direction.

Figure 4:
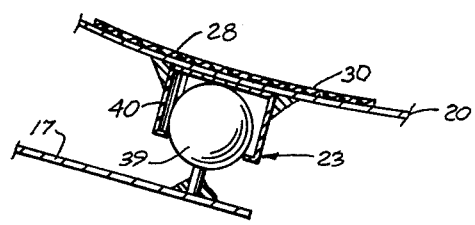
FIG. 4 is an enlarged fragmentary sectional view taken along line 4—4 in FIG. 1.

The mounting means 23 is shown in detail by FIG. 4. It is basically comprised of a ball 39 and a socket 40. The ball 39 is affixed to an outward end of the offset 37 while the socket 40 is similarly affixed to the underside of plate 20. The socket 40 pivotably receives the ball 39 and thereby permits free pivotal movement of the plates 20 and 21 about the center point of ball 39. This movement is relatively free and may be initiated through movement of the movable arm portion 13. Thus, the plates may be pivoted about the center of ball 39 in an up and down direction as indicated by the arrows in FIG. 2 or to the left or right as indicated by the arrows in FIG. 3, or a combination of any of the above movements may be performed. This flexibility is a greatly desired feature that is not provided by most conventional hand prostheses.

Prior to operation, the user places the glove 19 over the arm 11. He then positions the prosthesis with the elongated flange 32 engaged against the underside of the forearm such that the offset angular portion 37 extends beyond the joint area 12. He then affixes the flange 32 by buckling the straps 18 securely about the forearm in both places. The strap 24 may then be tightened about the movable arm portion 13. At this point the user may experimentally move the plates 20 and 21 together and apart to determine if the positioning of the prosthesis on the arm is correct. If not, the straps may be loosened and the prosthesis repositioned until a comfortable position is reached. At this point the prosthesis is ready for use.

During use, the user may apply force directly to the plate 21 or through the attached strap means 24 to close or open the plates to the positions shown in FIGS. 2 and 1 respectively. Furthermore, the plates may be pivoted up or down (even while remaining in the open position) or to the left or right through provision of the mounting means 23.

If an object is to be grasped, the user opens the plates, then brings the movable portion of the hand in a downward direction with respect to FIGS. 1 and 2 to bring the plates to the closed position as shown in FIG. 2. The object is thereby gripped between the plates 20 and 21 through the gripping force exerted between the relatively stationary base 17 and the movable arm portion 13.

It may have become apparent from the above description and attached drawings that various changes and modifications may be made therein. However, it is not the intent of the description and drawings to define the scope of what I claim to be my invention. The scope of my invention is set forth only in the following claims.

What I claim is:

1. A hand prosthesis for use with an arm having a functional joint and movable portion of the arm outward of the joint, comprising;

an elongated base member;

means on the base member for securely mounting the base member to a user in stationary relation to the movable arm portion;

first and second elongated plates having inward and outward ends;

hinge means pivotably joining the elongated plates at their inward ends;

mounting means pivotably connecting the first plate to the base member; and means fastened to the second plate for mounting the second plate to the movable portion of the arm.

2. The hand prosthesis as defined by claim 1 wherein forward ends of the plates include facing gripping surfaces that abut each other when they are held in a closed condition, and facing concave surfaces leading inwardly from the gripping surfaces to the hinge means.

3. The hand prothesis as defined by claim 1 wherein the mounting means is comprised of a ball and socket assembly.

4. The hand prosthesis as defined by claim 1 wherein the means on the base member include adjustable buckled straps mounted to the base member.

5. The hand prosthesis as defined by claim 1 further comprising glove means adapted to fit over a user's arm.

6. The hand prosthesis as defined by claim 1 further comprising a frictional covering on facing surfaces of the first and second plates.

7. The hand prosthesis as defined by claim 1 wherein:
the elongated base member includes an elongated flange mounting the first-named means and an integral offset portion at an outward end; and
wherein the mounting means connects the offset base portion and the first plate such that the plate may be located between the offset base portion and the movable arm portion when the prosthesis is mounted to a user's body.

8. The hand prosthesis as defined by claim 1 wherein the hinge means is located inward from the mounting means and said last-named means when mounted to a user's arm.

* * * * *